United States Patent [19]

Bueschken

[11] Patent Number: 4,885,397

[45] Date of Patent: Dec. 5, 1989

[54] PROCESS FOR THE PREPARATION OF CYCLIC KETONES BY ISOMERIZATION OF EPOXIDES

[75] Inventor: Wilfried Bueschken, Haltern, Fed. Rep. of Germany

[73] Assignee: Huels Aktiengesellschaft, Marl, Fed. Rep. of Germany

[21] Appl. No.: 244,070

[22] Filed: Sep. 14, 1988

[30] Foreign Application Priority Data

Dec. 24, 1987 [DE] Fed. Rep. of Germany ....... 3744094

[51] Int. Cl.$^4$ .............................................. C07C 45/51
[52] U.S. Cl. ..................................................... 568/341
[58] Field of Search .......................... 568/341, 310, 384

[56] References Cited

U.S. PATENT DOCUMENTS

| | | | |
|---|---|---|---|
| 3,255,258 | 6/1966 | Charles et al. | 568/384 |
| 3,321,515 | 5/1987 | Moore et al. | 568/341 |
| 3,855,303 | 12/1974 | Bishop | 568/341 |
| 4,734,529 | 3/1988 | Berg et al. | 568/341 |

FOREIGN PATENT DOCUMENTS

| | | | |
|---|---|---|---|
| 3136886 | 3/1983 | Fed. Rep. of Germany | 568/341 |
| 407874 | 5/1974 | U.S.S.R. | 568/341 |

*Primary Examiner*—James H. Reamer
*Attorney, Agent, or Firm*—Oblon, Spivak, McClelland, Maier & Neustadt

[57] ABSTRACT

A process for preparing a cyclic ketone from a cyclic epoxide, comprising the step of:
contacting a cyclic epoxide with an alkali or alkaline-earth halide salt in the presence of a polar solvent at a temperature ranging from 120° to 250° C., wherein said cyclic epoxide is unsubstituted or substituted with one or more $C_{1-5}$ alkyl or alkenyl groups, and wherein said cyclic epoxide comprises 7–20 ring carbon atoms, and contains up to 5 carbon-carbon multiple bonds.

14 Claims, No Drawings

PROCESS FOR THE PREPARATION OF CYCLIC KETONES BY ISOMERIZATION OF EPOXIDES

BACKGROUND OF THE INVENTION

1. Field of the Invention

The present invention relates to a process for the preparation of cyclic ketones by isomerization of the corresponding epoxides. More specifically, it relates to the rearrangement of the epoxide using an alkali or alkaline-earth halide in the presence of the a polar solvent.

2. Discussion of the Background

According to DE-PS 10 75 601, the isomerization of epoxides to the corresponding cyclic ketones is carried out in diethyl ether with anhydrous halides from group IIA and IIIA elements of the Periodic Table of Elements (designation corresponding to Chemical Abstracts), in particular with magnesium iodide and magnesium bromide. Following removal of the salts by means of a water bath, the ketones are obtained by distillation.

This process has the following disadvantages:
(a) depending on the substrate, the reaction times for a conversion greater than 95% are from 15 to 70 hours;
(b) the use of diethyl ether is very dangerous due to its low flash point, its high volatility, and its tendency to form explosive peroxides;
(c) the catalysts that are used are not recovered and pollute the waste water from the process.

Accordingly, there continues to be a need for a superior method of preparing cyclic ketones from the corresponding epoxides which does not use highly dangerous and flammable solvents, is not polluting and can be conducted on a relatively short time scale.

SUMMARY OF THE INVENTION

Accordingly, one the object of the present invention is a process for the preparation of cyclic ketones, which process is less time-consuming and can be carried out without risk and does not exhibit the aforementioned drawbacks.

This and other objects which will become apparent from the following specification have been achieved by the present process for preparing a cyclic ketone from a cyclic epoxide, which comprises contacting a cyclic epoxide with an alkali or alkaline-earth halide in the presence of a polar solvent at a temperature ranging from about 120°-250° C., wherein the cyclic epoxide is unsubstituted or substituted with one or more $C_{1-5}$ alkyl groups, and the cyclic epoxide comprises 7-20 ring carbon atoms and it may contain up to 5 carbon-carbon multiple bonds.

DETAILED DESCRIPTION OF THE PREFERRED EMBODIMENTS

The invention relates to a process for the preparation of cyclic ketones having 7 to 20 ring carbon atoms, having 0 to 5 multiple bonds, and having a side chain, which consists of 0 to 5 carbon atoms, of the corresponding epoxide (oxiranes) which can be practically and easily obtained from cyclic olefins.

For example, the process involves the preparation of the following compounds:

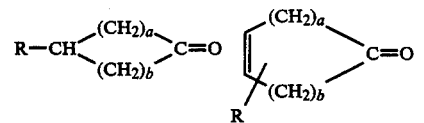

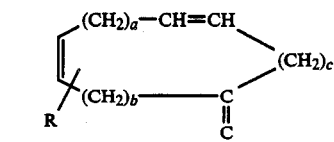

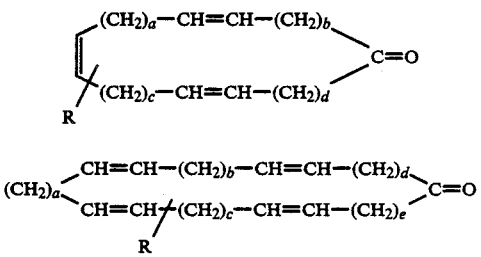

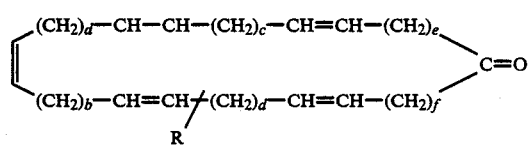

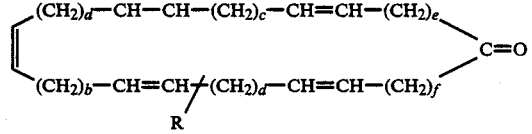

in which a, b, c, d, e, and f in each compound is selected in such a manner that the total number of ring carbon atoms ranges from 7 to 20 and R is a $C_{1-5}$ straight-chain or branched alkyl or alkenyl group such as for example H, $CH_3$, $C_2H_5$, $C_2H_3$, $C_3H_7$, $C_3H_5$, $C_4H_9$, $C_4H_7$, $C_5H_{11}$ or $C_5H_9$.

These ketones are, for example, useful intermediates in the preparation of lactams, amines, carboxylic acids and a large number of other compounds. Cyclic ketones having 15 to 17 carbon atoms are valuable for use in perfumes.

Surprisingly it has been found that epoxides, ranging from 120° to 250° C., in particular from 150° to 200° C., can be rearranged to the corresponding ketones in a polar solvent in the presence of alkali halides or alkaline-earth halides in very good yields and that the work-up and recovery of the solvent and catalyst is possible in practical, easy process steps.

It could not have been predicted and is surprising, that with the process of the present invention, despite the relatively high temperature, competing reactions such as aldehyde formation and ring contraction, formation of cyclic allyl alcohol derivatives, transannular hydrogen shifts, and with olefinic epoxides, the formation of bicyclic compounds, are negligibly low.

Suitable solvents are polar, aprotic solvents, which can form a homogenous solution with the alkali or alkaline-earth halide salt and the substrate and which do not undergo any reaction with the epoxides and the ketones resulting therefrom. Suitable solvents include N,N'-disubstituted cyclic ureas, N-substituted lactams and N,N'-disubstituted acid amides. The solvent quantity should be from 20 to 300% by weight, in particular from 80 to 120% by weight, based on the quantity of epoxide. Suitable catalysts are alkali halides and alkaline-earth halides such as magnesium iodide and magnesium bromide, preferably, sodium iodide and lithium chloride. As a rule, no more than 7 hours are required for complete reaction. The halide salts are added in quantities ranging from 0.5 to 20% by weight, preferably from 2 to 7% by weight, based on the quantity of epoxide.

The work-up is not complicated. The solvent is removed by means of distillation and the catalyst is filtered from the product ketone. The filtrate is washed with water and the dried. Catalyst and solvent are almost quantitatively recovered.

Compared to the known processes, the process of the invention has the following advantages:
(a) higher concentration of substrate and shorter reaction times, thus resulting in a significantly better space-time yield;
(b) use of a convenient, non-problematic solvent;
(c) recovery of the solvent and the added catalyst and, therefore, almost no salt load in the waste water.

Other features of the invention will become apparent in the course of the following descriptions of exemplary embodiments which were given for illustration of the invention and are not intended to be limiting thereof.

EXAMPLES

Example 1

25 g of epoxy-cyclododecane and 1 g of lithium chloride were dissolved in 20 g of N,N'-dimethyl ethylene urea and the solvent was stirred at 200° C. for 6 hours. The reaction mixture was analyzed to have a 94% yield of cyclododecanone.

Example 2

A solution containing 25 g of epoxy-cyclododecane, 1 g of lithium chloride, and 20 g of N-methyl-2-pyrrolidone was stirred at 200° C. for 6 hours. The reaction mixture contained 93.5% yield of cyclododecanone.

Example 3

A solution containing 12.5 g of 1,2-epoxy-cyclododeca-5,9-diene, 10 g of N,N'-dimethyl ethylene urea and 0.5 g of sodium iodide was stirred at 200° C. for 6 hours. The yield obtained by means of gas-chromatography was 95%.

Example 4

A solution containing 25 g of 1,2-epoxy-cyclododeca-5,9-diene, 20 g of N,N'-dimethyl ethylene urea and 1 g of lithium chloride was stirred at 200° C. for 6 hours. With a 90.7% conversion, the yield was 87.3%.

Example 5

A solution containing 25 g of 1,2-epoxy-cyclo- dodeca-5,9-diene, 20 g of N-methyl-2-pyrrolidone and 1 g of lithium chloride was stirred at 200° C. for 6 hours. With a 89.5% conversion, the yield was 87.3%.

Example 6

11.8 g of 1,2-epoxy-cyclohexadec-9-ene, 5 ml of N,N'-dimethyl ethylene urea and 0.5 g of sodium iodide were stirred at 200° C. for 6 hours. The result was 81% yield of cyclohexadec-8-en-1-one.

Example 7

A solution containing 500 g of 97.6% 1,2-epoxycyclohexadec-9-ene, 400 g of N,N'-dimethyl ethylene urea and 20 g of lithium chloride was stirred at 200° C. for 7 hours. The solvent was removed by distillation via a 20 cm long packed column (10 mbar; 106° C.). 390 g of N,N'-dimethyl ethylene urea was obtained as a 96.3% pure distillate. This corresponds to a recovery rate of 94%. After filtering off the lithium chloride by means of suction (19.72 g=98.6% of the feedstock), 300 g of toluene were added to the filtrate and washed three times with 100 ml water each time. After removal of toluene and emulsified water, 498 g of residue remained with a 90.5% content of cyclohexadec-8-enone. This corresponded to a yield of 92.3%.

Example 8

A solution containing 97.6% 1,2-epoxy-cyclo-hexadec-9-ene, 560 g of N-methyl-2-pyrrolidone and 28 g of lithium chloride was stirred at 200° C. for 7 hours. The solvent was removed by distillation via a 20 cm long packed column (14 to 16 mbar; head temperature 80° to 85° C.; bottom temperature 101° to 160° C.). 532 g of N-methylpyrrolidone having a 99.1% purity was obtained (94% of the feedstock). The precipitated lithium chloride (28g=100% of the feedstock) was filtered and washed with 300 g of toluene. The filtrate was extracted three times with 100 ml respectively (mixing time 5 minutes respectively, settling time 15 minutes respectively). After removal of toluene and emulsified water by means of distillation, 731 g of residue remained with a 89.6% content of cyclohexadec-8-en-1one (95.9% of the theoretical yield).

Example 9

10.5 g of epoxy-cyclohexadecane, 10 g of N,N-dimethyl ethylene urea and 0.5 g of lithium chloride were stirred at 200° C. for 6 hours. With a 100% conversion, a 98.5% yield of cyclohexadecanone was obtained.

Example 10

A mixture containing 10.5 g of epoxy-cyclohexadecane, 10 g of N-methylpyrrolidone, and 0.5 g of lithium chloride was stirred at 200° C. for 6 hours. With a 100% conversion, a 98.9% yield of cyclohexadecanone was obtained.

Obviously, numerous modifications and variations of the present invention are possible in light of the above teachings. It is therefore to be understood that within the scope of the appended claims, the invention may be practiced otherwise than as specifically described herein.

What is claimed and desired to be secured by letters patent of the United States is:

1. A process for preparing a cyclic keytone from a cyclic epoxide, comprising the step of:
contacting a cyclic epoxide with an alkali or alkaline-earth halide salt in the presence of a polar solvent selected from the group consisting of N,N'-disubstituted dialkyl carboxylic acid amides, N-substituted lactams, N,N,N',N'-tetrasubstituted ureas and N,N'-disubstituted cyclic ureas at a temperature ranging from 120° to 250° C., wherein said cyclic epoxide is unsubstituted or substituted with one or more $C_{1-5}$ alkyl or alkenyl groups, and wherein said cyclic epoxide comprises 7–20 ring carbon atoms, and contains 0–5 carbon-carbon multiple bonds.

2. The process of claim 1, wherein said salt is magneium halide, magnesium bromide, sodium iodide or lithium chloride.

3. The process of claim 1, wherein said salt is added in a quantity from 0.5 to 20% by weight, based on the epoxide.

4. The process of claim 3, wherein said salt is added in a quantity from 2-7 by weight based on the epoxide.

5. The process of claim 1, wherein said polar solvent is N-methyl-2-pyrrolidone or N,N'-dimethyl ethylene urea.

6. The process of claim 1, wherein the quantity of said solvent is from 20 to 300% by weight based on said epoxide.

7. The process of claim 6, wherein the quantity of said solvent is from 80 to 120% by weight based on said epoxide.

8. The process of claim 1, wherein said contacting step is preferably carried out at a temperature ranging from 150° to 200° C.

9. The process of claim 1, wherein said cyclic ketone has the formula shown below;

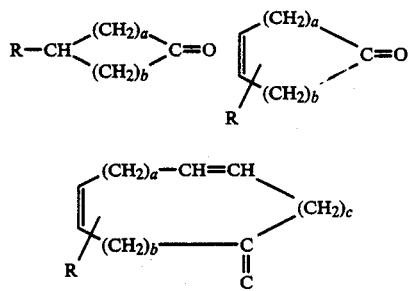
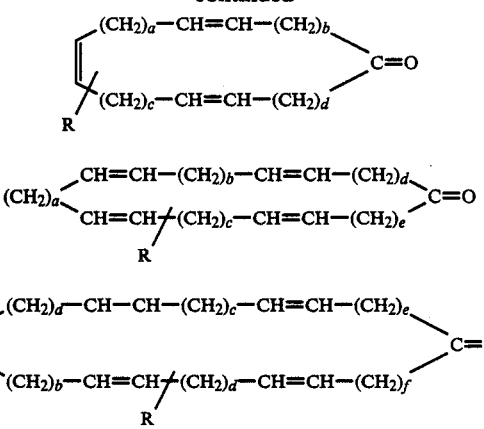

wherein a, b, c, d, e, and f are selected such that said cyclic ketone has from 7-20 ring carbon atoms, and wherein R is a $C_{1-5}$ straight-chain or branched alkyl or alkenyl group.

10. The process of claim 9, wherein R is H, $CH_3$, $C_2H_5$, $C_2H_3C_3H_7$, $C_3H_5$, $C_4H_9$, $C_4H_7$, $C_5H_{11}$ or $C_5H_9$.

11. The process of claim 10, wherein said cyclic ketone comprises from 15-17 carbon atoms.

12. The process of claim 1, further comprising removing said polar solvent and isolating said cyclic ketone.

13. The process of claim 12, wherein said solvent is removed by distillation and said cyclic ketone is isolated by filtration.

14. The process of claim 1, wherein said salt is lithium chloride.

* * * * *